United States Patent [19]

Dyroff et al.

[11] 4,289,753

[45] Sep. 15, 1981

[54] CALCULUS-INHIBITING METHOD AND COMPOSITIONS

[75] Inventors: David R. Dyroff; Gary F. Graf; Keun Y. Kim, all of St. Louis, Mo.; Walton F. Suchanek, Jr., Belleville, Ill.

[73] Assignee: Monsanto Company, St. Louis, Mo.

[21] Appl. No.: 784,188

[22] Filed: Apr. 4, 1977

[51] Int. Cl.$^3$ .............................................. A61K 9/68
[52] U.S. Cl. ....................................................... 424/48
[58] Field of Search ........................................... 424/48

[56] References Cited

U.S. PATENT DOCUMENTS

| | | | |
|---|---|---|---|
| 1,516,206 | 11/1924 | Pfanstiehl | 424/48 |
| 3,429,963 | 2/1969 | Shedlovsky | 424/48 |
| 3,542,917 | 11/1970 | Schwartz et al. | 424/48 |
| 3,920,837 | 11/1975 | Schmidt-Dunker et al. | 424/48 |
| 3,980,578 | 9/1976 | Nelson et al. | 424/48 |

FOREIGN PATENT DOCUMENTS

| | | | |
|---|---|---|---|
| 2411383 | 9/1974 | Fed. Rep. of Germany | 424/48 |
| 2108827 | 5/1972 | France | 424/48 |
| 995330 | 6/1965 | United Kingdom | 424/48 |
| 1373001 | 11/1974 | United Kingdom | 424/48 |
| 1376730 | 12/1974 | United Kingdom | 424/48 |

OTHER PUBLICATIONS

H. E. Schroeder et al., "Formation and Inhibition of Dental Calculus", 1969, pp. 3, 4, 7, 8, 25, 37-48 and 129-162.

*Primary Examiner*—Delbert R. Phillips
*Attorney, Agent, or Firm*—S. M. Tarter; W. H. Duffey; R. C. Griesbauer

[57] ABSTRACT

Oral compositions such as mouth washes, toothpastes, other oral hygiene products, foods, beverages, chewing gums and the like containing certain bis(carboxyalkoxy)-butanedioic acid compounds inhibit dental calculus formation.

7 Claims, No Drawings

CALCULUS-INHIBITING METHOD AND COMPOSITIONS

BACKGROUND OF THE INVENTION

The field of this invention is "oral compositions" which herein means products intended for introduction into the oral cavity in such a manner as to contact exposed dental surfaces therein. Examples of such products are animal foods and beverages, chewing gums and oral hygiene products including mouth washes, prophylaxis pastes, topical solutions and dentifrices such as toothpastes, tooth powders, dental creams and the like.

Dental calculus, or tartar as it is sometimes called, is a deposit which forms on surfaces of teeth predominantly at or near the gingival margin. Supragingival calculus appears most heavily in areas near the orifices of the salivary ducts. Mature calculus contains an inorganic portion which is largely calcium phosphate arranged in a hydroxyapatite crystal lattice structure similar to that occurring in bone, enamel or dentine. Also typically present is an organic portion consisting of desquamated epithelial cells, salivary sediment, food debris, various types of microorganisms, etc.

As calculus develops, it becomes white or yellowish unless stained or discolored by some extraneous substance. In addition to being undesirable from an esthetic standpoint, mature calculus deposits are sources of irritation of the gingiva and thereby a contributing factor to gingivitis and other diseases of the supporting structures of the teeth, the irritation decreasing the resistance of tissues to endogenous and exogenous organisms.

Periodic mechanical removal of this material by a dentist is routine dental office procedure. There have also been proposed a number of chemical agents for calculus removal. For example, alkali metal and ammonium diglycolates and diglycolates of organic bases such as urea, guanidine or ethanolamine are suggested for that use in U.K. Pat. No. 995,330 issued June 16, 1965 to R. A. Oetker. In French Pat. No. 2,108,827 published May 26, 1972 it is said that the calcium ion-sequestering capability of sodium gluconate can be used for removal of tartar from the teeth. In U.S. Pat. No. 1,516,206 issued Nov. 18, 1924 to C. Pfanstiehl it is said that a tartar solvent effect is provided by use of an aqueous solution of a lactone or anhydride of a weak organic hydroxy acid, e.g. galactonic acid, together with a weak organic acid such as maleic or citric acid, and it is taught in U.S. Pat. No. 3,429,963 issued Feb. 25, 1969 to L. Shedlovsky that dental calculus can be removed by use of dental preparations containing a hydrolyzed copolymer of ethylene and maleic anhydride having an average molecular weight of at least about 1500.

In some instances, chemical agents have been said to be capable of retarding calculus formation. For example, in U.S. Pat. No. 3,429,963 it is disclosed that a reduction in calculus formation was observed in rats when the drinking water given to the rats contained 1% of a hydrolyzed copolymer of ethylene and maleic anhydride. Another polymer, i.e., a polyester of a polycarboxylic acid having three or more carboxyl groups and a polyalkylene ether having at least two hydroxyl groups, is described as a calculus retarding agent in U.S. Pat. No. 3,542,917 issued Nov. 24, 1970 to A. M. Schwartz et al. In U.S. Pat. No. 3,920,837 issued Nov. 18, 1975 to M. Schmidt-Dunker et al it is said that tartar formation can be reduced by cyclohexanehexacarboxylic acid or its water-soluble salts, and in U.K. Pat. Nos. 1,373,001 and 1,373,003 issued Nov. 6, 1974 to R. Hoyles et al it is said that calculus can be reduced by use of a dentifrice containing a sparingly water-soluble zinc salt, e.g. zinc citrate. Various phosphorous compounds such as, e.g., ethane-1-hydroxyl-1,1-diphosphonic acid (hereinafter EHDP) have also been proposed for such use in U.S. Pat. No. 3,488,419 issued Jan. 6, 1970 to H. W. McCune et al.

Some of the chemical agents heretofore proposed for calculus removal or retardation contain functional groups of uncertain effect on animals in terms of toxicity, side effects, etc. Certain other kinds of compounds containing only carbon, hydrogen, oxygen and possibly pharmaceutically acceptable cations are believed essentially free from such uncertainty and therefore preferable for use in oral compositions. Also desirable for present purposes are compounds of relatively simple structure and low molecular weight, as well as compounds which can be prepared without resort to a polymerization process. Accordingly, oral compositions containing compounds which meet those criteria and substantially inhibit dental calculus formation are highly desirable, and it is an object of this invention to provide such compositions. Another object is a method for inhibiting dental calculus formation by use of such compositions. Other objects will be apparent from the following disclosure in which percentages are by weight except where otherwise noted.

SUMMARY OF THE INVENTION

This invention provides an oral composition effective in inhibiting formation of dental calculus, said composition comprising (1) a bis(carboxyalkoxy)-butanedioic acid compound selected from the group consisting of acids having the structural formula:

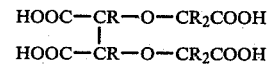

wherein R is hydrogen or lower alkyl, and pharmaceutically acceptable salts of said acids and (2) a carrier suitable for use in the oral cavity, said compound being present in said composition in amount and concentration sufficient to substantially inhibit formation of dental calculus. Also provided by this invention is a method for inhibiting formation of dental calculus by introducing such an oral composition into an oral cavity containing exposed dental surfaces. In preferred embodiments, the oral composition in which such a calculus-inhibiting compound is employed in accordance with this invention is selected from the group consisting of oral hygiene products, foods, beverages and chewing gums.

DESCRIPTION OF PREFERRED EMBODIMENTS

In the foregoing formula each R can be the same as or different from any other R in that formula. Also as used herein, "lower alkyl" means $C_1$-$C_4$ alkyl which can be branched (e.g. isopropyl, isobutyl or tert-butyl) or cyclic (cyclopropyl or cyclobutyl) or straight-chain (methyl, ethyl, n-propyl or n-butyl). In many embodiments of the invention it is preferred that R in the foregoing formula is hydrogen or normal alkyl, and in some of those embodiments it is even more preferred that R is hydrogen, methyl or ethyl. It is preferred that at least one R in each —CR$_2$— radical in that formula is hydrogen, and it is generally even more preferred that each R in each —CR$_2$— radical is hydrogen. In some embodiments it is preferred that the R in at least one of the

radicals in that formula is hydrogen, and it is usually even more preferred that the R's in both of such

radicals are hydrogen. In an embodiment of particular preference, each R in the foregoing formula is hydrogen. Each of these embodiments is preferable on the basis of relatively low molecular weight. On the other hand, some compounds similar to those expressly included in that formula but wherein at least one of the R's in that formula contains more than four carbon atoms may similarly inhibit calculus formation when used in suitable oral compositions and in such cases should be regarded as equivalents of said bis(carboxyalkoxy)-butanedioic acid compounds for purposes of this invention.

The compound represented by the foregoing formula when R is hydrogen is herein designated 2,3-bis(carboxymethoxy)butanedioic acid (hereinafter for conveninece called BCMBDA). The tetrasodium salts of that acid and other bis(carboxyalkoxy)butanedioic acid (hereinafter for convenience called BCMBDA). The tetrasodium salts of that acid an other bis(carboxyalkoxy)butanedioic acids represented by the foregoing formula when the R in each

radical in that formula is hydrogen and at least one R in a —CR$_2$— radical in that formula is lower alkyl can be prepared by procedure set forth in U.S. Pat. No. 3,980,578 issued Sept. 14, 1976 to G. E. Nelson et al, the disclosure of which is incorporated herein by reference. Briefly, that patent teaches the reaction of an α-diazo ester containing up to seven carbon atoms in the carboxyl structure and a tartrate ester followed by saponification of the resulting product. The sodium salts of other bis(carboxyalkoxy)-butanedioic acids represented by the foregoing formula when the R in at least one

radical in that formula is lower alkyl can be prepared by procedure analogous to that in U.S. Pat. No. 3,980,578 but in which there is used instead of the tartrate ester reactant suggested in that patent a di($C_1$-$C_4$ alkyl) ester of an appropriate tartaric acid derivative having a lower alkyl substituent on either or both of the hydroxylated carbon atoms in that derivative. Such derivatives of tartaric acid can be prepared by procedure analogous to that disclosed in U.S. Pat. No. 3,852,306 issued Dec. 3, 1974 to John N. Rapko, the disclosure of which is incorporated herein by reference.

Alternatively, the tetrasodium salts of BCMBDA and other bis(carboxyalkoxy)-butanedioic acids represented by the foregoing formula can be prepared by conventional ether producing reactions such as a Williamson ether synthesis in which one molecule of a conjugate base of a dialkyl ester of tartaric acid or a derivative thereof having a lower alkyl substituent on either or both of the hydroxylated carbon atoms in that derivative is reacted with two molecules of a bromo- or iodocarboxylate having the structural formula ZCR$_2$COOX in which Z is Br or I, R is hydrogen or lower alkyl and X is methyl or ethyl, and then saponification of the resulting tetracarboxylic acid ester with sodium hydroxide. A reaction temperature between −20° and 100° C. is usually satisfactory for the halocarboxylate/conjugate base reaction, and an elevated or atmospheric pressure is normally also employed.

Any of the aforementioned bis(carboxyalkoxy)-butanedioic acid salts can be converted to the corresponding acid (e.g. BCMBDA) by treatment with a strong acid, e.g. HCl, $H_2SO_4$ or a strongly acidic ion exchange resin. Other metal salts of the resulting acids can be prepared by neutralization with the appropriate metal hydroxide, e.g. an alkali metal hydroxide such as potassium hydroxide. The corresponding ammonium, mono- or di ($C_1$-$C_3$ alkyl) ammonium or mono- or di($C_1$-$C_3$ alkanol) ammonium salts can be prepared by treating such acids with ammonia, an appropriate alkylamine or alkanolamine or hydroxide thereof in accordance with procedures known in the art.

In the oral compositions of this invention, the proportions in which the bis(carboxyalkoxy)-butanedioic acid compounds are present as acids and/or partially-substituted or fully-substituted salts thereof are dependent on the pH of the composition. That pH is normally between about 4 and about 11, although in some instances it may be higher or lower than that range. Below about pH 4 there is a greater possiblity of damage to dental enamel despite the relative safety of the aforementioned acid or its salts. Above about pH 11, greater difficulty is encountered in formulating products having satisfactory flavor and mildness. A preferred pH range is from about 6 to about 10. In many embodiments, the pharmaceutically acceptable salts employed are preferably water-soluble salts such as, e.g., sodium, potassium or ammonium salts, to facilitate their dissolution in saliva.

As aforesaid, some embodiments of this invention are oral hygiene products such as dentifrices, mouth washes, prophylaxis pastes and topical solutions. A dentifrice, especially toothpaste, containing a calculus-inhibiting amount of an acid represented by the foregoing formula and/or a pharmaceutically acceptable salt thereof is a preferred embodiment of this inventon. A mouth wash containing such an acid and/or salt is another preferred embodiment. Except for inclusion of a bis(carboxyalkoxy)-butanedioic acid compound as aforesaid, many formulations of such products are well known in the art. For example, typical formulations of toothpastes and mouth washes compatible with calculus-inhibiting compounds of the kind employed in accordance with this invention are described in U.S. Pat. Nos. 3,639,569 issued Feb. 1, 1972 to R. F. Medcalf, Jr., 3,544,678 issued Dec. 1, 1970 to W. J. Griebstein, 3,678,154 issued July 18, 1972 to J. S. Widder et al and 3,959,458 issued May 25, 1976 to F. O. Agricola et al, the disclosures of which are incorporated herein by reference.

Under conditions of normal use, the oral compositions of this invention are pharmaceutically acceptable, i.e., capable of introduction into the oral cavity without significant adverse effect on tooth structure or other injury to health. Subject to the limits of such acceptability, the calculus-inhibiting amounts and concentrations of the bis(carboxyalkoxy)-butanedioic acid compounds can be varied widely in the oral compositions of this invention. Such amounts and concentrations are also readily definable for each kind of oral composition by formulators skilled in the art. Generally, concentrations from 0.01% to about 10% are preferred. Oral compositions which in ordinary usage may be accidentally or intentionally ingested can contain relatively low but still highly effective concentrations. Of course, any such ingested composition should be physiologically (i.e., digestively acceptable. Thus, a mouth wash in accordance with this invention typically contains between about 0.1 and about 3% of the aforementioned calculus-inhibiting compound. Dentifrice compositions, topical solutions and prophylaxis pastes, the last normally administered professionally, may desirably contain up to about 10% or even more thereof but usually contain between about 0.1 and about 5% and even more typically between about 1 and about 2% thereof.

While it is not intended that this invention be limited to any particular theory ofoperation, it appears that the bis(carboxyalkoxy)-butanedioic acid compounds inhibit calculus formation by interfering with the conversion of dissolved calcium phosphate in saliva to crystalline deposits in the nature of calcium hydroxyapatite. Hence the compositions of this invention preferably do not contain soluble polyvalent cations in an amount likely to deplete the crystal growth inhibiting capacity of those compounds to the extent that their calculus formation inhibiting activity would be essentially neutralized.

The following specific examples are illustrative only and do not imply any limitations on the scope of the invention.

EXAMPLES I-V

A. Evaluations of Calculus Inhibition

Evaluations of the effectiveness of compounds employed in accordance with this invention to inhibit calculus formation were carried out fundamentally as described in "A Method and Apparatus for Studying In Vitro Calculus" by S. Yankelowitz et al of the Colgate-Palmolive Co., Journal of Dental Research 44 (No. 4), 648–53 (1965). In accordance with that method, now well known in the art, simulated oral calculus deposits are caused to be formed on glass slides by mechanically rotating the slides edgewise and vertically at 0.5 rpm in such a way that each slide passes alternately through a small sample of whole human saliva containing 0.1% of added monocalcium phosphate and then through a forced draft of air which at least partially dries each slide before it passes again through that saliva sample. As stated in the journal article just mentioned, the resulting calculus deposits have been found similar to oral calculus deposits in both composition and X-ray diffraction pattern.

In the present evaluations, 150 mls of stimulated saliva were collected over a three-day period (50 ml/day) from a donor whose saliva had been previously found to have a substantial tendency toward calculus formation. The collected saliva was also of a type in which, under the conditions of this test, calculus formation is inhibited by EHDP substantially more than by water substituted for the EHDP in a comparative test run. Each 50 ml portion of the saliva was kept frozen until ready for use. At that time the combined 150 ml sample was neutralized to pH $7\pm0.05$ after addition of the 0.1% of monocalcium phosphate, thoroughly stirred and then divided into 25 ml aliquots. To one aliquot was added 1 ml of a 0.1 M solution of the tetrasodium salt of BCMBDA, and to a second aliquot was added 1 ml of a 0.1 M solution of the prior art anti-calculus compound EHDP, each of those solutions having been previously neutralized with NaOH or $H_2SO_4$. To a third aliquot was added 1 ml of distilled water.

For comparative test purposes, the three aliquots were then placed in identical side-by-side trough-like containers in an oven equipped with apparatus adapted to rotate a separate set of three $22\times40$ mm glass slides (spaced about 120° apart in relation to the rotating shaft on which they were mounted) through each of the saliva containers and to maintain a steady horizontal flow of air against the slides and perpendicular to the axis of their rotation. All slides used were essentially identical and mounted on the shaft such that the same portion (24 mm) of the length of each slide passed through the appropriate saliva sample.

In the oven just described, the calculus formation test was continued for 20 consecutive hours with the interior of the oven maintained at $37°\pm1°$ C. and a relative humidity between 76 and 78%. The saliva samples were then removed from the oven, after which rotation of the slides in the flow of air was continued for an additional hour before removal of the slides from the oven. The weight of each slide and any deposit remaining thereon was then compared with the weight of the slide prior to its use in this test, and visual appraisals of the deposits were made using photographs taken of each slide under identical conditions to further eliminate variables from those appraisals. Results were recorded separately for each of the three slides in each set and then averaged. Thereafter, the entire procedure was repeated using saliva from a different donor and the results of the two runs were averaged to provide the results reported hereinafter.

In these tests it was found that the weights of simulated calculus on the slides that had been exposed to the salivas containing the tetrasodium salt of BCMBDA averaged 0.13 mg, those on the slides used in the comparative runs with EHDP averaged 0.23 mg, and those on the slides used in the comparative runs with water averaged 0.57 mg. Thus in the runs using the BCMBDA salt, formation of the simulated calculus averaged 43% less than in the comparative runs using EHDP and 77% less than in the comparative runs using water. In the visual appraisals, the amounts of opaque material deposited on the slides that had been exposed to the salivas containing the BCMBDA salt were judged to be, on average, much less than half as great as those on the slides used in the comparative runs with water and substantially below 25 on an essentially linear scale in which 100 represents the amount of opaque material on the slides used in the comparative runs with water and 0 represents the amount of such material deposited on the slides used in the comparative runs with EHDP.

B. Preparation of Oral Compositions

The compound tested in Part A of these examples, the corresponding acid and other pharmaceutically acceptable salts of that acid are useful for inhibition of dental calculus formation when incorporated in compatible carriers or vehicles of any of the usual types. The following are examples of mouth wash compositions comprising at least one of such compounds.

| Component | Examples | | | |
|---|---|---|---|---|
| | I | II | III | V |
| | Parts by Weight | | | |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | .045 | .045 | .02 |
| Sodium Cyclamate | 0.75 | 0.75 | 0.75 | .04 |
| Flavor | .088 | .088 | .088 | .088 |
| Salt of BCMBDA | [2]3.0 | [3]4.0 | [4]2.0 | [5]1.8 |
| pH[6] | 7.0 | 7.0 | 8.5 | 10.0 |

[1]Polyoxyethylene (20 moles of ethylene oxide) sorbitan monooleate - a nonionic emulsifier supplied by Atlas Powder Co.
[2]Tetrammonium salt.
[3]Tetra(triethanolammonium) salt.
[4]Tetrasodium salt.
[5]Tetrapotassium salt.
[6]Adjusted to value indicated with NaOH or H$_2$SO$_4$.

The following is an example of a toothpaste composition comprising at least one of such compounds.

| Component | Example V Parts by Weight |
|---|---|
| Water | 31.58 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |
| BCMBDA | 1.00 |
| pH[2] | 5.90 |

[1]Prepared in accordance with U.S. Pat. No. 3,112,247 granted November 26, 1963.
[2] Adjusted to indicated pH with sodium hydroxide.

Other examples of toothpaste compositions comprising at least one of said bis(carboxyalkoxy)-butanedioic acid compounds are substantially identical to the toothpaste composition above except for substitution of the corresponding potassium or ammonium salt of BCMBDA or the sodium, potassium or ammonium salt of 2,3-bis(1-carboxyethoxy)-butanedioic acid, 2,3-diethyl-2,3-bis(carboxymethoxy)-butanedioic or 2,3-dimethyl-2,3-bis(1-carboxyethoxy)-butanedioic acid.

Additional examples of oral compositions comprising at least one of such compounds include other mouth washes and toothpastes, tooth powders, dental creams and prophylaxis pastes for use by a dentist in polishing of teeth after removal of calculus deposits. Examples of such compositions, except for inclusion of a calculus-inhibiting compound of the kind used in accordance with the present invention, are described in U.S. Pat. Nos. 3,544,678, 3,639,569, 3,678,154 and 3,959,458. Typically, toothpastes are aqueous compositions containing a polishing agent, a surfactant, a binder, a humectant, a preservative, flavoring and sweetening agents and optionally therapeutic agents. Mouth washes typically contain water, ethanol, flavoring, sweetening and coloring agents and optionally a surfactant. Other examples or oral compositions comprising at least one of the compounds used in accordance with this invention include human foods and beverages such as soft drinks, candies, pastries, etc., foods for pets or livestock, chewing gums, etc. Such beverages, as distinguished from mere drinking water, typically contain a flavoring agent, a nutrient or sweetening agent, and optionally therapeutic agents. Chewing gums typically contain base materials, plasticizers or softeners, sugar or other suitable carbohydrates such as glucose, sorbitol, etc. Sugarless gums may contain other sweetening agents such as saccharin or sodium cyclamate. The ingredients of each of the foregoing oral compositions, other than said bis(carboxyalkoxy)-butanedioic acid) compounds, as well as various mixtures of such ingredients, are illustrative of carriers suitable for use in the oral cavity in accordance with the present invention.

The embodiments of this invention in which an exclusive property or privilege is claimed are defined as follows:

1. An oral composition effective in inhibiting formation of dental calculus, said composition comprising (1) a bis(carboxyalkoxy)-butanedioic acid compound selected from the group consisting of acids having the structural formula:

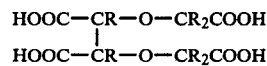

wherein R is hydrogen or lower normal alkyl and each R can be the same as or different from any other R in said formula, and pharmaceutically acceptable salts of said acids and (2) a carrier suitable for use in the oral cavity, said compound being present in said composition in amount and concentration sufficient to substantially inhibit formation of dental calculus, said composition being selected from the group consisting of oral hygiene products and chewing gums.

2. A composition according to claim 1 wherein each R in said formula is hydrogen and said composition being selected from the group consisting of oral hygiene products.

3. A composition according to claim 1, said compound being selected from the group consiting of alkali metal and ammonium salts of said acids.

4. a composition according to claim 3 said composition being selected from the group consisting of toothpastes having a pH between about 4 and about 11, said concentration being between about 0.1% and about 5% by weight of said composition.

5. A method for inhibiting formation of dental calculus which comprises introducing into an oral cavity containing exposed dental surfaces a composition according to claim 1.

6. A method for inhibiting formation of dental calculus which comprises introducing into an oral cavity containing exposed dental surfaces a composition according to claim 3.

7. A method of inhibiting formation of dental calculus which comprises introducing into an oral cavity containing exposed dental surfaces a composition according to claim 2.

* * * * *